US012758230B2

(12) United States Patent
Okada

(10) Patent No.: US 12,758,230 B2

(45) Date of Patent: Oct. 13, 2026

(54) ENDOSCOPIC TREATMENT TOOL

(71) Applicant: ZEON CORPORATION, Tokyo (JP)

(72) Inventor: Noriaki Okada, Tokyo (JP)

(73) Assignee: Zeon Corporation, Tokyo (JP)

( * ) Notice: Subject to any disclaimer, the term of this patent is extended or adjusted under 35 U.S.C. 154(b) by 88 days.

(21) Appl. No.: 18/552,389

(22) PCT Filed: Mar. 10, 2022

(86) PCT No.: PCT/JP2022/010471
§ 371 (c)(1),
(2) Date: Sep. 25, 2023

(87) PCT Pub. No.: WO2022/209691
PCT Pub. Date: Oct. 6, 2022

(65) Prior Publication Data

US 2024/0173036 A1 May 30, 2024

(30) Foreign Application Priority Data

Mar. 31, 2021 (JP) ................................ 2021-061441

(51) Int. Cl.
*A61B 17/30* (2006.01)
*A61B 17/122* (2006.01)
(Continued)

(52) U.S. Cl.
CPC ...... *A61B 17/1285* (2013.01); *A61B 17/1227* (2013.01); *A61B 2017/00367* (2013.01); *A61B 17/30* (2013.01)

(58) Field of Classification Search
CPC ............ A61B 17/1285; A61B 17/1227; A61B 2017/00367; A61B 2017/00269;
(Continued)

(56) References Cited

U.S. PATENT DOCUMENTS 4,312,363 A * 1/1982 Rothfuss .................. G01B 3/20 600/587
4,467,802 A 8/1984 Maslanka
(Continued)

FOREIGN PATENT DOCUMENTS

CN 111818859 A 10/2020
EP 1604614 A1 12/2005
(Continued)

OTHER PUBLICATIONS

Extended European Search Report issued in European Patent Application No. 22779914.5, dated Feb. 19, 2025 in 11 pages.
(Continued)

*Primary Examiner* — Kathleen S Holwerda
*Assistant Examiner* — James R McGinnity
(74) *Attorney, Agent, or Firm* — Knobbe, Martens, Olson & Bear, LLP

(57) ABSTRACT

To prevent the loop member from passing through the opening/closing portion and to provide an endoscopic procedure tool capable of securely cutting the loop member by the opening/closing portion, the clip device 10 has a connection hook 11 that protrudes from the inner sheath 12 to open the pair of arm portions 11*a* and 11*b* by its own elasticity, and closes the pair of arm portions 11*a* and 11*b* by being buried in the inner sheath 12. The connection hook 11 has claw portions 11*a*1 and 11*b*1 at the ends of the arm portions 11*a* and 11*b*, which clip a portion of the endoscopic traction clip 1 connected with the loop member 4 and enable it to be retracted into the inner sheath 12 as it is pulled in the inner sheath 12. A gap at the closest portion between the pair of claw portions 11*a*1 and 11*b*1 when the pair of arm portions 11*a* and 11*b* are buried in the inner sheath 12 and closed has a specified value that prevents the loop member
(Continued)

from passing through, when a part of the loop member 4 is clipped between the pair of claw portions 11$a$1 and 11$b$1.

3 Claims, 25 Drawing Sheets

(51) Int. Cl.
*A61B 17/128* (2006.01)
*A61B 17/00* (2006.01)

(58) Field of Classification Search
CPC . A61B 17/0218; A61B 17/282; A61B 17/128; A61B 17/10; A61B 17/00234; A61B 17/28; A61B 17/1006; A61B 17/0483; A61B 17/083; A61B 17/122; A61B 17/29; A61B 2017/0034; A61B 1/00; A61B 17/0487
See application file for complete search history.

(56) References Cited

U.S. PATENT DOCUMENTS

| | | | | |
|---|---|---|---|---|
| 5,100,418 | A * | 3/1992 | Yoon | A61B 17/0487 606/151 |
| 8,419,751 | B2 | 4/2013 | Harada et al. | |
| 11,083,465 | B2 * | 8/2021 | Ryan | A61B 17/083 |
| 2003/0083747 | A1 * | 5/2003 | Winterbottom | A61F 2/4455 623/17.11 |
| 2006/0224165 | A1 * | 10/2006 | Surti | A61B 17/29 606/142 |
| 2006/0259049 | A1 | 11/2006 | Harada et al. | |
| 2016/0000433 | A1 * | 1/2016 | Raybin | A61B 17/00234 606/145 |
| 2016/0213375 | A1 | 7/2016 | Rosenberg et al. | |
| 2017/0281176 | A1 * | 10/2017 | Maekubo | A61B 17/1285 |
| 2019/0099172 | A1 * | 4/2019 | Wales | A61B 1/018 |
| 2021/0106335 | A1 | 4/2021 | Sugitani et al. | |
| 2022/0183670 | A1 * | 6/2022 | Montenegro | A61B 17/068 |
| 2022/0249087 | A1 * | 8/2022 | Diduch | A61B 17/06004 |
| 2023/0165590 | A1 * | 6/2023 | Camisa | A61B 17/1227 606/112 |
| 2023/0346409 | A1 * | 11/2023 | Matsuo | A61B 17/0218 |

FOREIGN PATENT DOCUMENTS

| | | | |
|---|---|---|---|
| EP | 3689254 | A1 | 8/2020 |
| JP | 10-118013 | A | 5/1998 |
| JP | 2008-532637 | A | 8/2008 |
| JP | 2010-81970 | A | 4/2010 |
| JP | 2012-200518 | A | 10/2012 |
| WO | WO 2004/082488 | A1 | 6/2006 |
| WO | WO 2019/131713 | A1 | 7/2019 |
| WO | WO 2020/121394 | A1 | 6/2020 |
| WO | WO 2019/066084 | A1 | 11/2020 |

OTHER PUBLICATIONS

International Search Report and Written Opinion of the International Searching Authority for International Application No. PCT/JP2022/010471, mailed on May 17, 2022, in 7 pages.
International Search Report for International Application No. PCT/JP2022/010471, mailed on May 17, 2022 (English translation), in 2 pages.
International Search Report and Written Opinion of the International Searching Authority for International Application No. PCT/JP2022/013564, mailed on Jun. 7, 2022, in 7 pages.
International Search Report for International Application No. PCT/JP2022/013564, mailed on Jun. 7, 2022 (English translation), in 2 pages.

* cited by examiner

ENDOSCOPIC TREATMENT TOOL

CROSS-REFERENCE TO RELATED APPLICATIONS

This application is the U.S. National Phase under 35 U.S.C. § 371 of International Application PCT/JP2022/010471, filed Mar. 10, 2022, which claims priority to JP Application No. 2021-061441, filed Mar. 31, 2021.

FIELD OF THE INVENTION

The present invention relates to an endoscopic treatment tool for performing treatment on body tissue by an in vitro manipulation using an endoscope, and more specifically, to an endoscopic treatment tool in which a connection hook for connecting a medical clip also serves to cut a loop member carried into the body by the medical clip.

BACKGROUND ART

A clip device as an endoscopic treatment tool is used to indwell the medical clip connected to the tip of the sheath which is passed through the treatment guide tube of an endoscope, while clipping body tissue for hemostasis, marking, etc., for example during an endoscopic submucosal dissection (ESD), by operation of an operation portion attached to a rear end of the sheath.

Conventional clip devices of this type are known to have a connection hook (open/close portion) attached to the distal end of a drive wire inserted into a sheath. The connection hook has a pair of arms arranged in a substantially V shape with respect to each other and a U-shaped portion connecting their base end sides. By sliding the sheath toward the proximal end with respect to the drive wire, the hook protrudes from the distal end of the sheath and opens its legs by its own elasticity, and by sliding toward the distal end, it buries itself within the distal end of the sheath and closes its legs (see, for example, Patent Document 1).

In the clip device disclosed in Patent Document 1, the connection hook is used not only to connect medical clips and transport them into the body to grasp (clipping) body tissue, so that there is no need to separately prepare a cutting tool for cutting the loop member, thereby making it possible to reduce the cost required for the treatment.

CITATION LIST

Patent Literature

[Patent Document 1] International Publication No. 2019/066084

SUMMARY OF THE INVENTION

Technical Problem

In the clip device disclosed in Patent Document 1 (hereinafter referred to as a clip device according to the prior art), when cutting a loop member by a connection hook (opening/closing portion), first, a portion of the loop member is clipped between the claws of each of the pair of arms of the opening/closing portion, and in this state, the pair of arm portions is pulled into the sheath together with the loop member (see FIGS. 8A and 8B of Patent Document 1). After that, the pair of arm portions and the loop member are pulled further inside the sheath, and at that time, the loop member is cut by the shearing force that accompanies the pulling while the peripheral surface of the loop member touches the inner diameter of the sheath. (same, see FIG. 8C).

As an example, FIG. 18 shows a procedure for cutting the loop member 95 by the opening/closing portion 90 in the conventional clip device 100. As shown in FIG. 18, in the conventional clip device 100, a loop member 95 is partially clipped between the tip portions (claw portions 90*b*, 90*b*) of a pair of arm portions 90*a*, 90*a* of the opening/closing portion 90 (see FIG. 18A), in the process of drawing the pair of arm portions 90*a* and 90*a* into the sheath 92 together with the loop member 95 in that state (see FIGS. 18B and 18C), the loop member 95 could pass through between the respective claw portions 90*b* and 90*b* of the pair of arms 90*a* and 90*a*.

As one of the reasons for this, it is mentioned that, in the clip device 100 according to the prior art, the opening/closing portion 90 is configured to fulfill its original function, which is not for cutting the loop member 95, such as connecting a medical clip, clipping body tissue, and the like, and after the ESD operation, no measures such as determining the value of the gap between the claw portions 90*b*, 90*b* are taken so that the loop member 95 does not pass through when the loop member 95 is cut.

As a result, in the conventional clip device 100, during the series of operations shown in FIG. 18 for cutting the loop member 95, the opening/closing portion 90 is pulled into the inner sheath 92 while clipping the loop member 95 (see FIG. 18B). Furthermore, in the process of drawing the loop member 95 further into the inner sheath 92, the loop member 95 may pass through between the claw portions 90*b*, 90*b* of the opening/closing portion 90 (see FIG. 18C). There was a problem that it was not possible to reliably perform the cutting of the loop member 95.

The present invention has been made in view of the above problems, and is aimed to provide an endoscopic treatment tool that prevents a loop member from passing through an opening/closing portion and that can reliably cut the loop member by the opening/closing portion.

Means to Solve the Problem

In order to achieve the above object, the endoscopic treatment tool according to the present invention comprises: a tubular sheath; an operation portion provided at a proximal end of the sheath and allows an operation wire inserted through the sheath to slide with respect to the sheath; and an opening/closing portion constituted by an elastic body having a pair of arm portions attached at a distal end of the operation wire and arranged so as to open each other in a substantially V shape as it goes to its tip, the opening/closing portion protruding from the distal end of the sheath to open the pair of arm portions by its own elasticity by sliding the sheath towards a proximal side with respect to the operation wire, the opening/closing portion being buried in the distal end of the sheath to close the pair of arm portions by sliding the sheath towards the distal end side with respect to the operation wire, wherein the opening/closing portion has a pair of claw portions at the tip of each of the pair of arm portions that are bent in a closing direction and that can pull a clip connected to a loop member into the sheath by holding a part of the clip during a movement to bury the opening/closing portion in the sheath, a gap at the closest portion between the pair of claw portions when the pair of arm portions are buried in the sheath and closed has a specified value that prevents the loop member from passing through, when a part of the loop member is clipped between the pair of claw portions.

According to the above configuration, it is possible to provide an endoscopic treatment tool capable of securely cutting the loop member by preventing the loop member from passing through, in the process of accommodating a portion of the loop member between the pair of claw portions and burying it into the sheath.

Further, in the endoscopic treatment tool according to the present invention, the opening/closing portion may be so configured that a first claw portion of the opening/closing portion, which is the claw portion of one arm portion of the pair of arm portions, is bent from its base end portion by a predetermined diameter, a second claw portion of the opening/closing portion, which is the claw portion of the other arm portion, is bent from its base end portion by a diameter longer than the first claw portion and larger than the predetermined diameter, the pair of arm portions are closed in such a manner that the second claw portion covers the first claw portion from the outside, in a state of being buried in the sheath, the closest portion is formed between the protruding end portion of the first claw portion and the region between the protruding portion of the second claw portion and the base end portion.

According to the above configuration, it is possible to prevent the first claw portion and the second claw portion from interfering with each other when the pair of arm portions are buried in the sheath and the legs are closed, so that it is possible to realize an endoscopic treatment tool capable of reliably cutting the loop member without interfering with the movement when the tool is buried in a sheath and the legs are closed.

Further, in the endoscopic treatment tool according to the present invention, the specified value may be 0.15 mm or less.

According to the above configuration, even in a situation where the loop member is extended by the tension applied to the loop member in the process of retracting a part of the loop member between the pair of claw portions into the sheath, it is possible to realize an endoscopic treatment tool capable of reliably cutting the loop member by preventing the passing through from the loop member.

Further, in the endoscopic treatment tool according to the present invention, the opening/closing portion may be a connection hook that releasably connects a medical clip indwelled while clipping body tissue.

According to the endoscopic treatment tool having the above-described configuration, the clip that is indwelled while clipping body tissue can be preferably used as a clip device having a connection hook that releasably connects a medical clip provided as the opening/closing portion.

BRIEF DESCRIPTION OF THE DRAWINGS

FIG. 14 is completed, and the tip of the clip device is brought close to cut the loop member.

DETAILED DESCRIPTION OF EMBODIMENTS

Hereinafter, embodiments of the present invention will be described with reference to the drawings. In order to make the structure of each part of the tool easy to understand, the relative size of each part in each drawing does not necessarily correspond to the exact size of the actual tool.

An endoscopic treatment tool according to an embodiment of the present invention is a tool that uses an endoscope to treat body tissue by manipulation outside the body, is operable in a state of protruding from the tip of the sheath and in a state of being buried in the sheath, as a mechanism for performing the above treatment, and has an opening/closing portion that opens in a substantially V shape when protruding from the tip of the sheath and closes when buried in the sheath.

Hereinafter, as an example, a case where the endoscopic treatment tool according to the present embodiment is applied to a clip device provided with a connection hook for releasably connecting a medical clip that is indwelled by clipping body tissue will be described below.

<Configuration of Clip Device>

First, the configuration of the clip device according to the present embodiment will be described with reference to FIG. 1 to FIG. 6.

Figure 1:
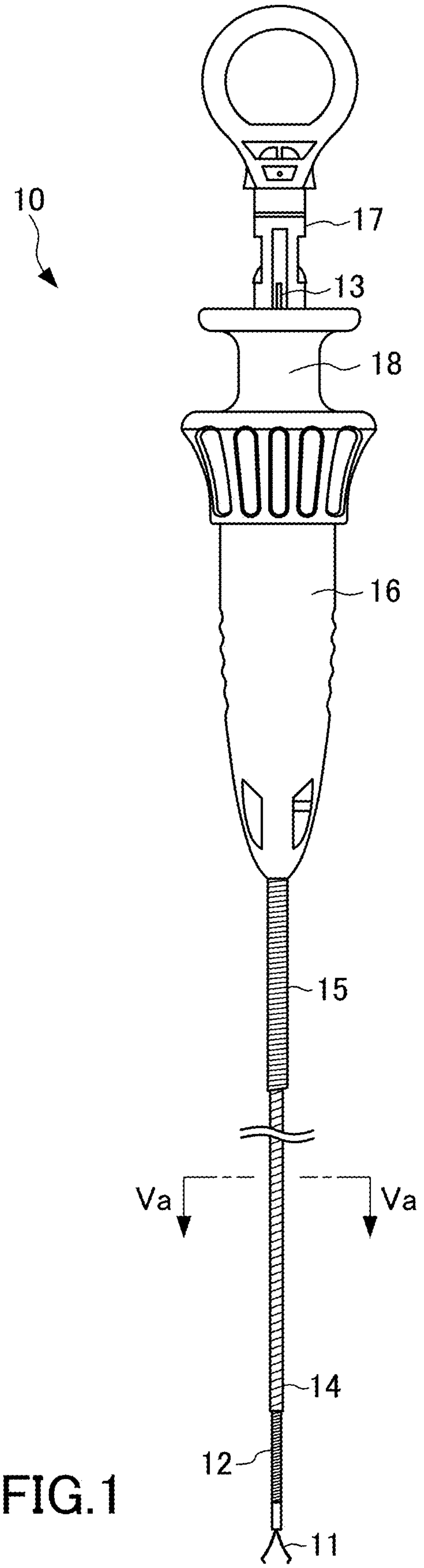
FIG. 1 is a diagram showing the appearance of a clip device according to an embodiment of the present invention.
Figure 2:
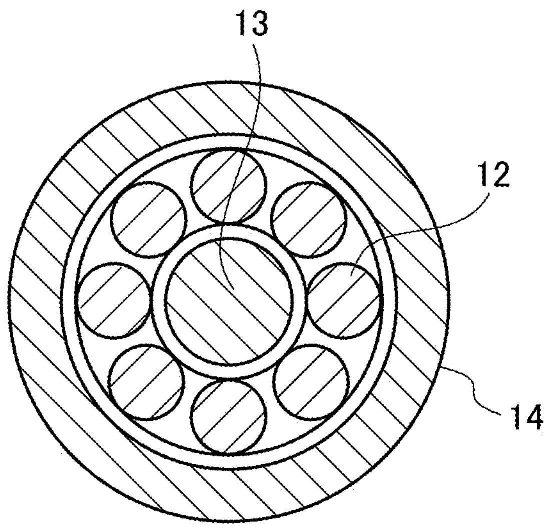
FIG. 2 is a cross-sectional view taken along line Va-Va in FIG. 1.

As shown in FIG. 1, the clip device 10 generally includes a connection hook 11, an inner sheath 12, an operation wire 13, an outer sheath 14, a reinforcement coil 15, a slider 16, a base portion 17, and an operation portion 18.

A tubular inner sheath 12 is inserted through the tubular outer sheath 14, and an operation wire 13 is inserted through the inner sheath 12. The inner sheath 12 is slidable within the outer sheath 14, and the operation wire 13 is slidable within the inner sheath 12.

The outer sheath 14 is constituted by a flexible hollow tube, and a coil tube is used in the present embodiment. As the coil tube, a flat wire coil tube formed by spirally winding a long flat plate made of metal (stainless steel) or the like can be used. However, a round wire coil tube or an inner flat coil tube may instead be used. The inner diameter of a tip portion of the outer sheath 14 is about 2 to 3 mm.

The inner sheath 12 is constituted by a flexible hollow tube, and a wire tube is used in the present embodiment. The wire tube is a hollow stranded tube formed by twisting a plurality of wires (cables) made of, for example, metal (stainless steel) or the like into a hollow spiral. As the inner sheath 12, a wire tube may be mainly used, and only a tip side portion thereof may be a coil tube. The inner diameter of the tip portion of the inner sheath 12 is about 1.5 to 2.5 mm.

The operation wire 13 is constituted by a flexible wire, and a wire rope is used in the present embodiment. A wire rope is a stranded rope formed by twisting a plurality of wires (cables) made of, for example, metal (stainless steel) or the like into a spiral shape. However, as the operation wire 13, a wire tube similar to the inner sheath 12 may be used.

Figure 3:
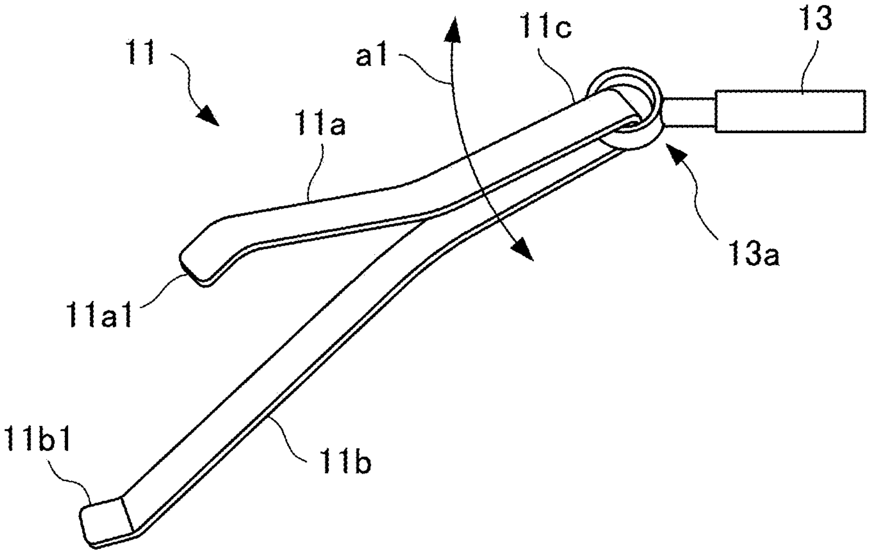
FIG. 3 is a perspective view showing a configuration of a connection hook and its vicinity of the clip device of FIG. 1.

The connection hook 11 arranged at the tip of the sheath of the clip device 10 has a pair of arm portions 11*a* and 11*b* made of elastic body arranged in a substantially V shape toward the tip thereof, as shown in FIG. 3. By cooperating with the inner sheath 12, the pair of arm portions 11*a* and 11*b* can take two states of an opened state and a closed state. Claw portions 11*a*1 and 11*b*1 are formed at the tip portions of the arm portions 11*a* and 11*b* of the connection hook 11 by bending them inward (toward sides facing each other), respectively, so that the connecting portion 21 of the clip body 2 is clipped to be connected.

The base end portion of the connection hook 11 is a U-shaped portion 11*c* that is continuous with the base end portions of the pair of arm portions 11*a* and 11*b* and formed in a substantially U shape. The arm portions 11*a* and 11*b* including the claw portions 11*a*1 and 11*b*1 and the U-shaped portion 11*c* can be formed by appropriately bending (plastically deforming) one elongated plate material made of an elastic body. Although not particularly limited, the plate material forming the connection hook 11 has a thickness of about 0.20 to 0.24 mm and a width of about 0.6 mm. Stainless steel, for example, is used as the plate material.

An annular member 13*a* formed in a substantially annular shape is integrally welded and fixed to the tip (distal end) of the operation wire 13 slidably inserted into the inner sheath 12 by laser welding or the like. The annular member 13*a* has an outer diameter of about 1.2 mm and an inner diameter of about 0.8 to 1.0 mm.

The connection hook 11 is inserted through the annular member 13*a* and arranged so that the U-shaped portion 11*c* is loosely fitted in the annular member 13*a*, so as to be attached to the distal end of the operation wire 13 thereby making it possible to swing. By attaching the connection hook 11 to the tip of the operation wire 13 through the annular member 13*a* and the U-shaped portion 11*c* loosely fitted to the annular member 13*a*, the connection hook 11 can freely rotate in the direction of arrow a1 in FIG. 3. The connection hook 11 constitutes the opening/closing portion of the present invention.

Returning to FIGS. 1 and 2, the vicinity of the base end (proximal end) side of the outer sheath 14 is inserted into the reinforcement coil 15 and integrally fixed to the reinforcement coil 15. The reinforcement coil 15 is integrally fixed to the slider 16, and the distal end side portion of the base portion 17 is inserted into the slider 16. The slider 16 is slidable with respect to the base portion 17 between two positions, a position moved toward the tip (distal end) side and a position moved toward the base end (proximal end) side.

An operation portion 18 is slidably held on the base portion 17, and the inner sheath 12 is fixed to the base portion 17. A base end of the operation wire 13 is fixed to the operation portion 18.

When the operation portion 18 is slid toward the tip end side (distal end side) with respect to the base portion 17, the inner sheath 12 is retracted into the operation wire 13, and the connection hook 11 at the distal end of the operation wire 13 protrudes from the tip of the inner sheath 12 and opens its legs by its own elasticity. When the operation portion 18 is slid toward the base end side (proximal end side) with respect to the base portion 17, the operation wire 13 is retracted into the inner sheath 12, and the connection hook 11 at the distal end of the operation wire 13 is pulled into the inner sheath, so that while entering the inner sheath 12, the legs are gradually closed, and by being buried in the inner sheath 12, the legs are completely closed.

When the slider 16 is slid to the base end side position with respect to the base portion 17, the inner sheath 12 can be protruded from the tip of the outer sheath 14. On the contrary, when the slider 16 is slid to the tip side position with respect to the base portion 17, the tip of the inner sheath 12 can be retracted (buried) in the outer sheath 14.

<Configuration of Connection Hook>

The configuration of the connection hook 11 of the clip device 10 will be described in more detail.

Figure 4A:
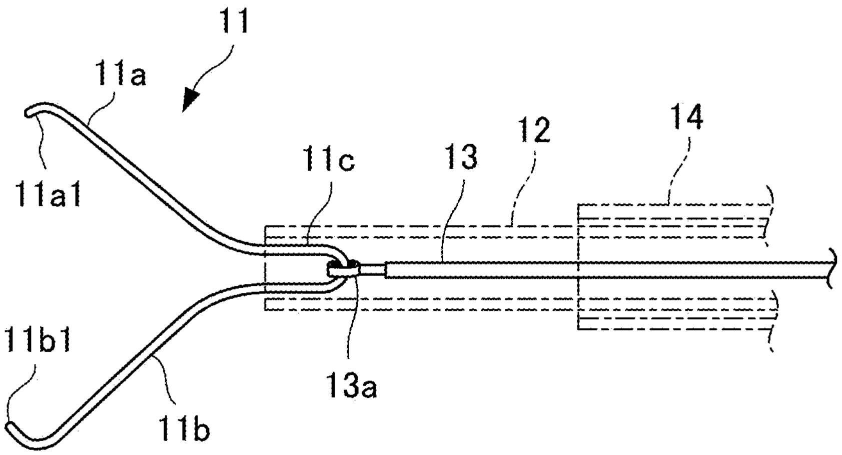
FIG. 4A is a diagram showing a state in which the connection hooks of the clip device of FIG. 1 are protruded.
Figure 4B:
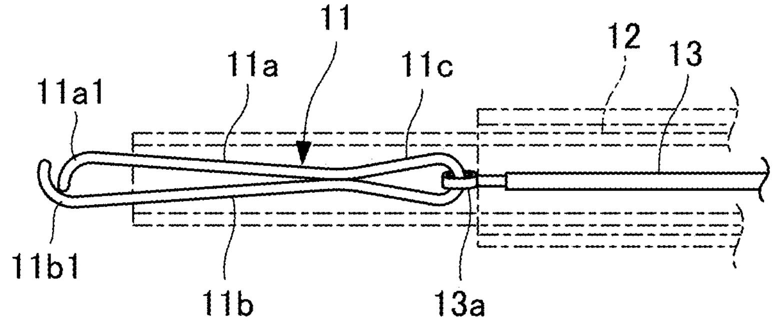
FIG. 4B is a diagram showing a retracted state of the connection hook of the clip device of FIG. 1.

FIGS. 4A and 4B are diagrams showing the operating state of the connection hook 11 of the clip device 10 of the present embodiment. Here, FIG. 4A shows a state in which the connection hook 11 of the clip device 10 is protruded by an operation of sliding the operation portion 18 to the tip side (distal end side) with respect to the base portion 17, while FIG. 4B shows a state in which the connection hook 11 of the clip device 10 is gradually closed while being inserted into the inner sheath 12 by the operation of sliding the operating portion 18 toward the base end side (proximal end side) with respect to the base portion 17. Thus, in the clip device 10, the connection hook 11 protrudes from the distal end of the inner sheath 12 by sliding the inner sheath 12 to the proximal end side with respect to the operation wire 13, and opens the legs by its own elasticity. Then, by sliding the inner sheath 12 to the distal end side with respect to the operation wire 13, the legs are buried in the distal end of the inner sheath 12 and closed.

Figure 5:
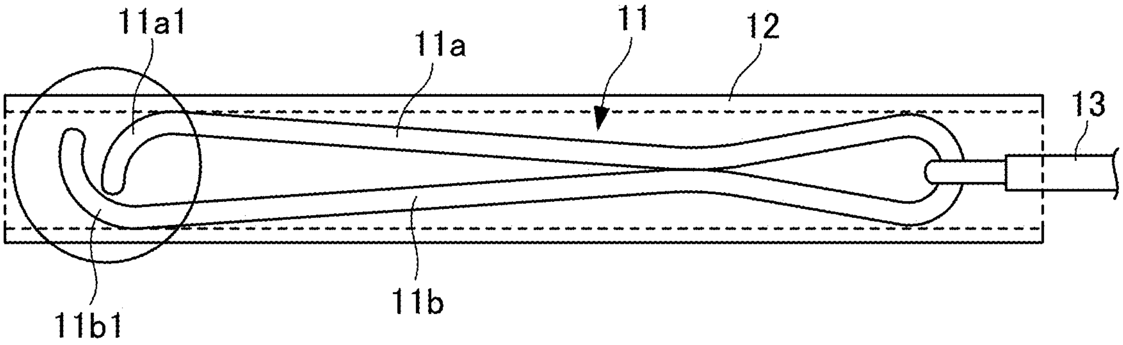
FIG. 5 is a conceptual diagram showing the configuration of the inner sheath and the connection hook in the retracted state shown in FIG. 4B as viewed from the side.
Figure 6:
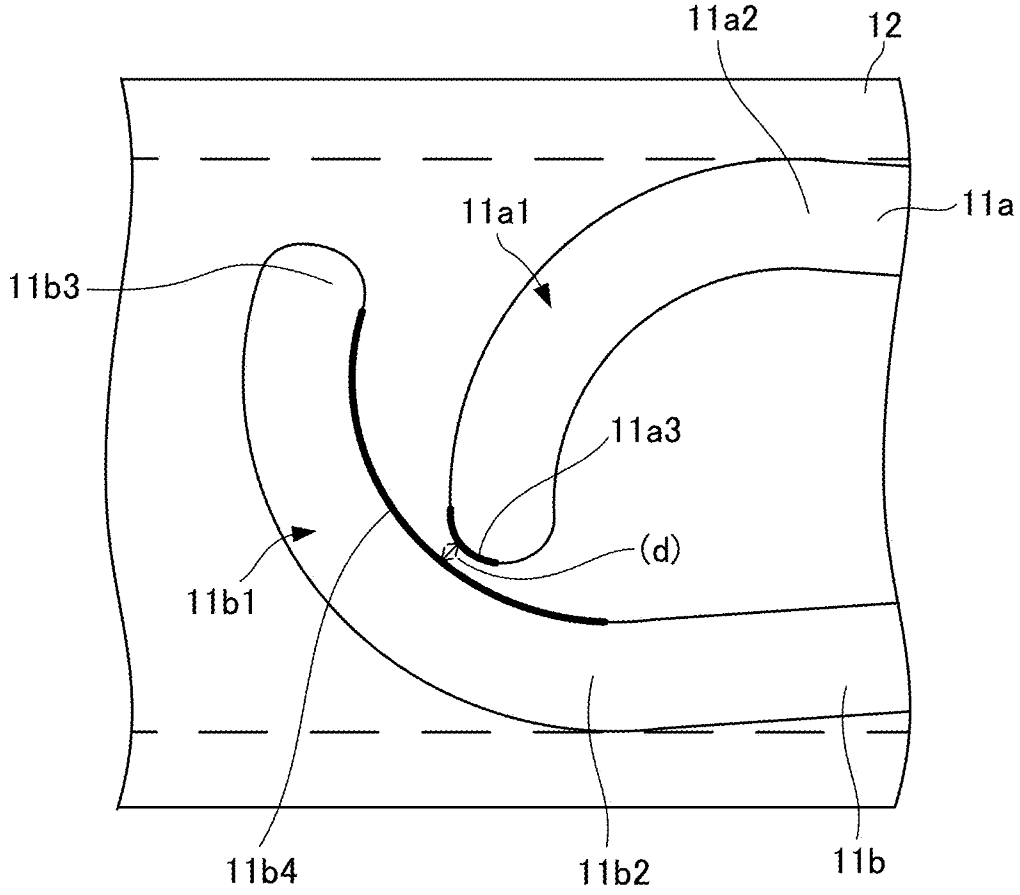
FIG. 6 is an enlarged view showing the configuration within the circle in FIG. 5.

FIG. 5 is a conceptual diagram showing the configuration of the inner sheath 12 and the connection hook 11 viewed from the side in a state where the connection hook 11 is retracted further into the inner sheath 12 from the state shown in FIG. 4B. FIG. 6 is an enlarged view of the configuration of the inner sheath 12 and the connection hook 11 shown in the circle of FIG. 5.

As shown in FIGS. 4A, 4B, 5 and 6, the connection hook 11 has a claw portion **11*a*1 of one arm portion 11*a* of the pair of arm portions 11*a* and 11*b* extending from its base end portion 11*a*2 by a predetermined diameter, and the claw portion 11*b*1 of the other arm portion 11*b* is bent from its base end portion 11*b*2 to a shape that is longer than the claw portion 11*a*1 of the arm portion 11*a* and has a larger diameter than the claw portion 11*a*1. The claw portion 11*a*1 of the arm portion 11*a* and the claw portion 11*b*1 of the arm portion 11*b*** constitute a first claw portion and a second claw portion of the present invention, respectively.

Further, when the connection hook 11 is buried in the inner sheath 12 as shown in FIG. 6, the pair of arm portions **11*a* and 11*b* are closed so that the claw portion 11*b*1 covers the claw portion 11*a*1 from the outside, and a portion is formed between a protruding end portion 11*a*3 of a claw portion 11*a*1 of one arm portion 11*a* and a region 11*b*4 on the bent side between the protruding end portion 11*b*3 of the claw portion 11*b*1 of the other arm portion 11*b* and the base end portion 11*b*2 (the region between the protruding end portion and the base end portion of the second claw portion) where they are closest to each other. Here, the distance d between the closest point of proximity between the protruding end portion 11*a*3 of the claw portion 11*a*1 of one arm portion 11*a* and the region 11*b*4 on the bent side of the claw portion 11*b*1 of the other arm portion 11*b* (the gap between the claw portion 11*a*1 and the claw portion 11*b*1**) is designed to be, for example, 0.15 mm or less.

The gap d (=0.15 mm or less) described above is the value set forth so that the loop member 4, partly clipped by the claw portion **11*a*1 of the arm portion 11*a* and the claw portion 11*b*1 of the arm portion 11*b*, is prevented from passing through between the claw portion 11*a*1 and the claw portion 11*b*1, when the connection hook 11 is used to cut the loop member 4 (see FIG. 7) of the endoscopic traction clip 1, which will be described later, after a lesion is exfoliated by ESD (see FIG. 15), The above-described cutting of the loop member 4 of the endoscopic traction clip 1 is performed by the procedure shown in FIGS. 16A, 16B, and 16C. In this procedure, first, a portion of the loop member 4 is clipped between the claw portions 11*a*1 and 11*b*1 of the pair of arm portions 11*a* and 11*b*, and the connection hook 11 is retracted into the inner sheath 12 together with the loop member 4 in this state. In the process of retracting the connection hook 11 into the inner sheath 12 together with the loop member 4, the clip device 10 operates the connection hook 11 in such a way that, for example, the claw portions 11*a*1 and 11*b*1 of the pair of arm portions 11*a* and 11*b* are retracted into the inner depth of the inner sheath 12 through the positions shown in FIG. 17**.

Figure 16A:
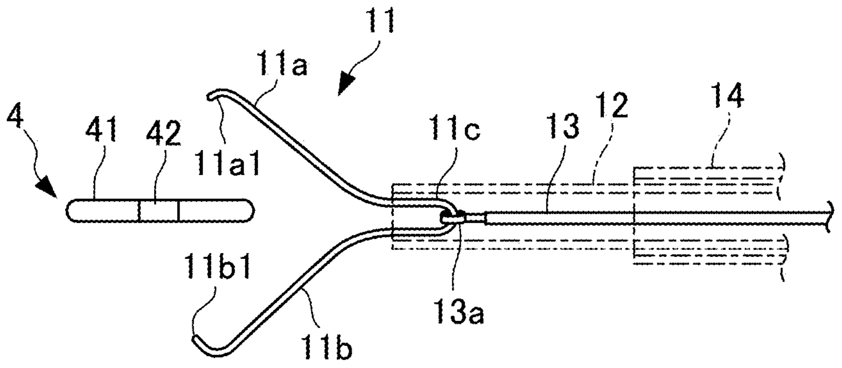
FIG. 16A is a view showing a step of cutting the loop member of the traction clip of FIG. 7, showing a state in which the tip of the clip device is arranged near the loop member and the connection hook is protruded.
Figure 16B:
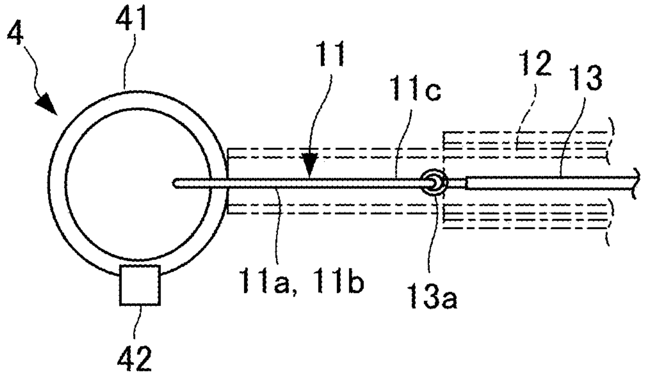
FIG. 16B is a view showing the step of cutting the loop member of the traction clip of FIG. 7, and in the subsequent step of FIG. 16A, part of the loop member is clipped by the connection hook and the connection hook is pulled from the tip of the sheath, bringing the loop member into contact with the distal end of the inner sheath.
Figure 16C:
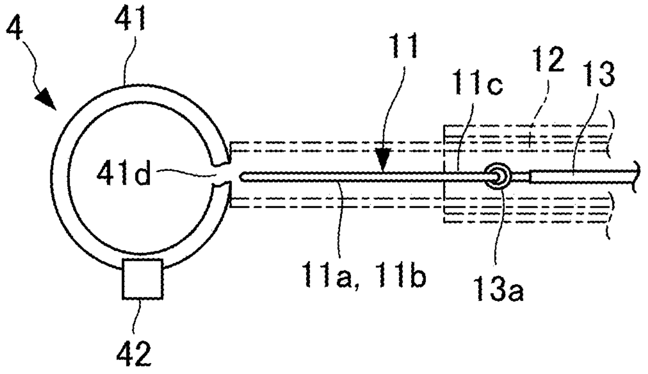
FIG. 16C is a view showing the step of cutting the loop member of the traction clip of FIG. 7, and in the subsequent step of FIG. 16B, the connection hook is further retracted from the tip of the inner sheath and the loop member is cut by the force generated on the loop member by the tip of the inner sheath and the connection hook.
Figure 17:
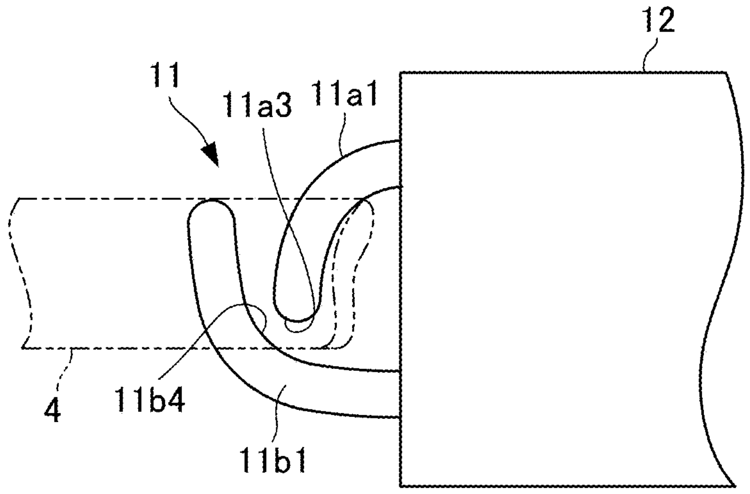
FIG. 17 is a diagram showing leg closing mode between a pair of claw portions when the connection hook of the clip device according to the embodiment of the present invention is pulled into the sheath.
Figure 18A:
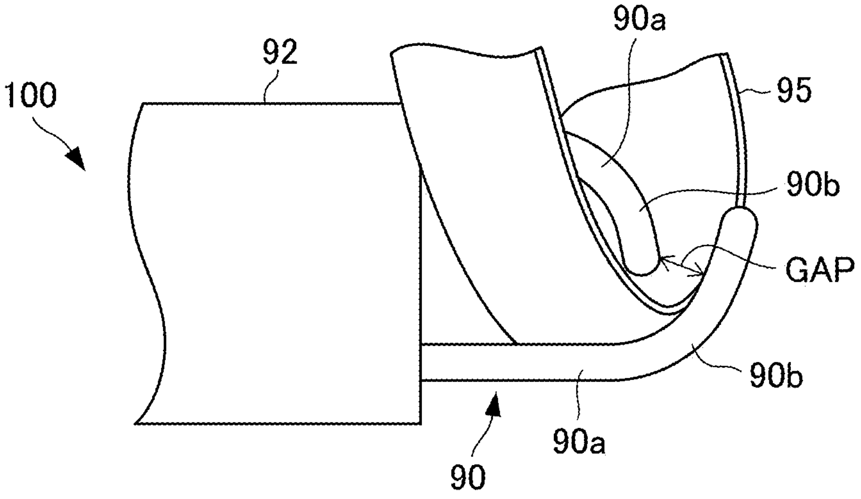
FIG. 18A is a diagram for explaining the occurrence of the loop member passing through in the process of cutting the loop member of a traction clip with the connection hook of a conventional clip device, and a state is shown in which a portion of the loop member is clipped by the connection hook and the loop member is brought into contact with the distal end of the inner sheath.
Figure 18B:
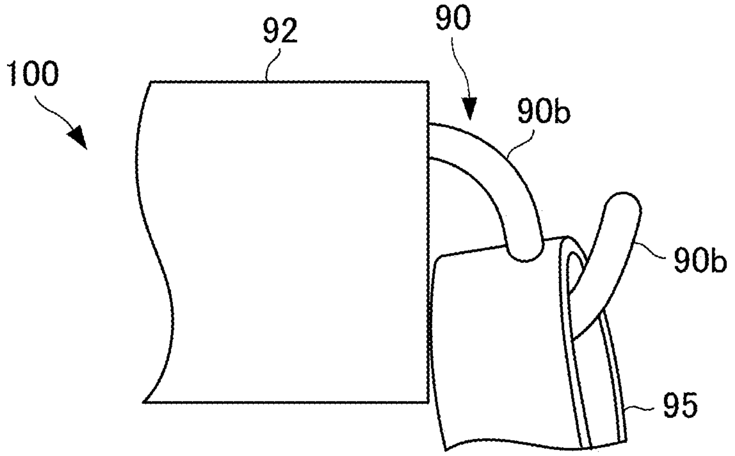
FIG. 18B is a view for explaining the occurrence of the loop member passing through in the process of cutting the loop member of a traction clip with the connection hook of a conventional clip device, and the connection hook is pulled from the tip of the inner sheath from the state of FIG. 18A, and it shows a further pulled state.
Figure 18C:
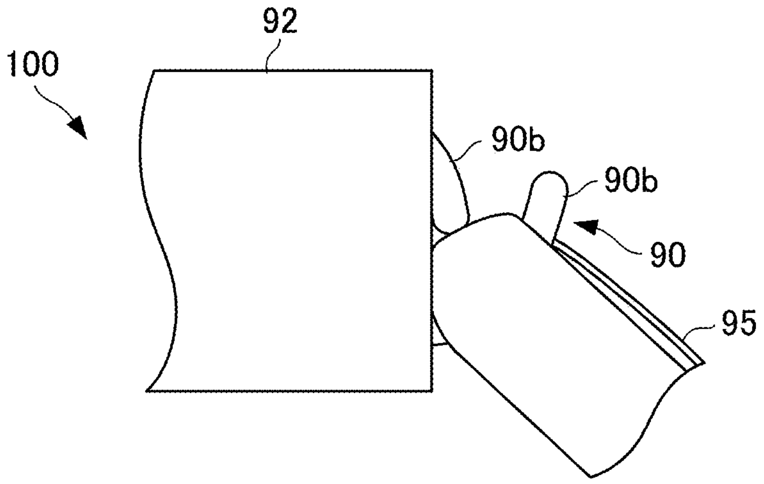
FIG. 18C is a view for explaining the occurrence of the loop member passing through in the process of cutting the loop member of a traction clip with the connection hook of a conventional clip device, and the connection hook is pulled from the tip of the inner sheath from the state of FIG. 18B, and it shows a further pulled state.

For example, when the claw portions **11*a*1 and 11*b*1 of the pair of arm portions 11*a* and 11*b* are accommodated at the position shown in FIG. 17, the separation distance between the claw portions 11*a*1 and 11*b*1 of the pair of arm portions 11*a* and 11*b* is extremely close to the value (=d) of the gap between the closest portions shown in FIG. 6. At that time, the loop member 4 is stretched to the state indicated by the dotted line in FIG. 17, but the cross-sectional diameter is kept larger than the distance between the claw portions 11*a*1 and 11*b*1, so that the loop member 4 does not pass through between the claw portions 11*a*1 and 11*b*1 until the cutting is completed. Cutting of the loop member 4 will be described later in detail with reference to FIGS. 16A, 16B, 16C and 17**.

<Configuration of Endoscopic Traction Clip>

Figure 7:
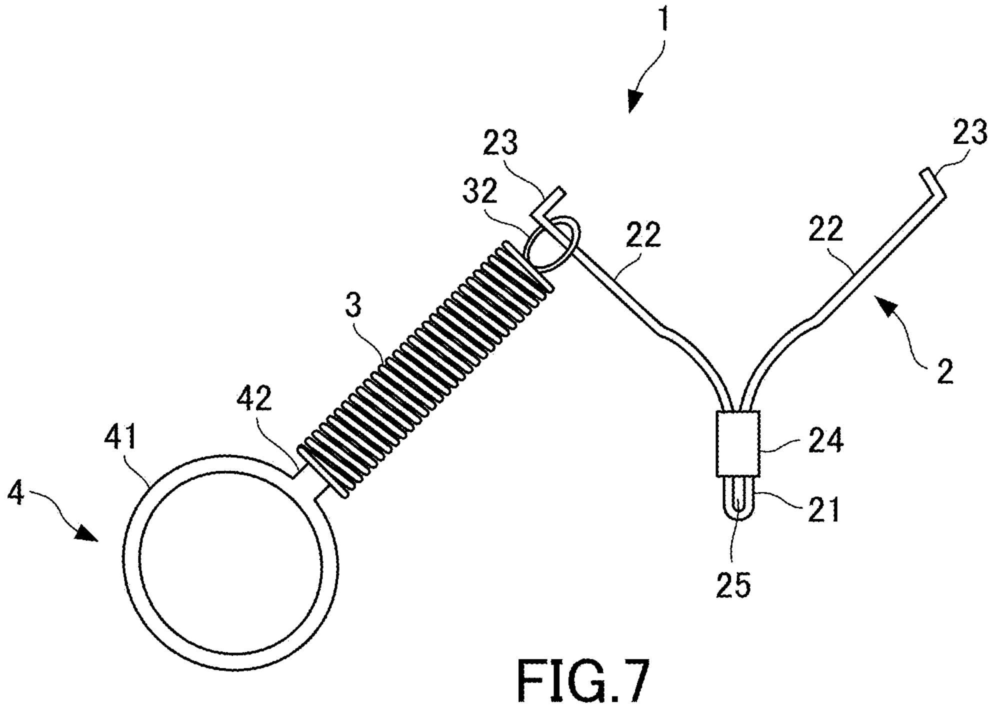
FIG. 7 is a diagram showing the overall configuration in a state where the arm portions of the clip body of the traction clip for endoscope used in the clip device of the embodiment of the present invention are opened.
Figure 8:
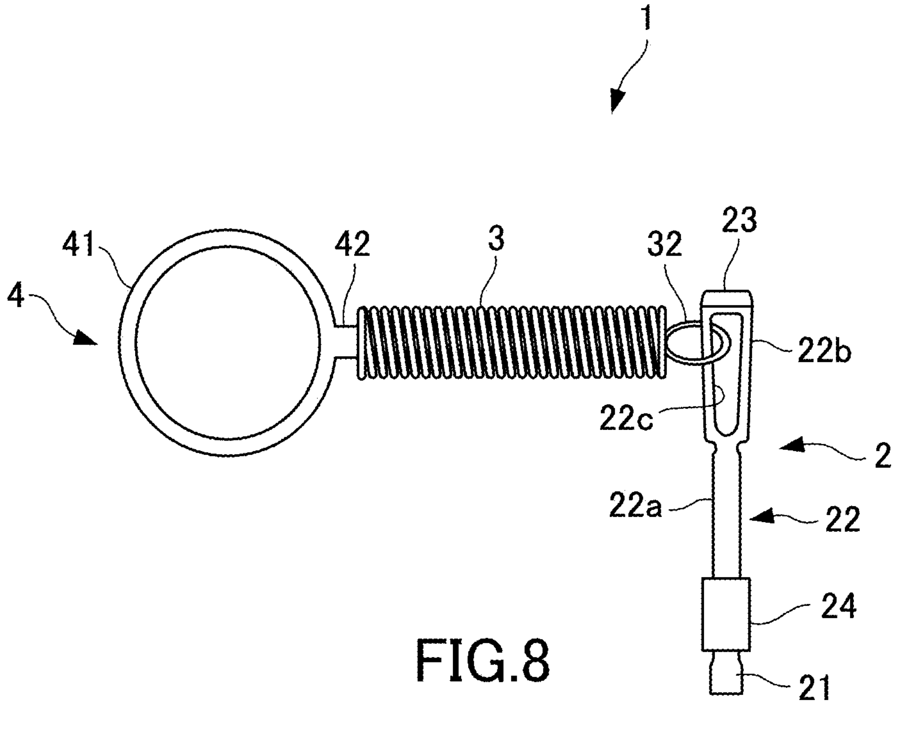
FIG. 8 is a diagram showing a clip body, which constitutes the traction clip of FIG. 7 in a different orientation.
Figure 9:
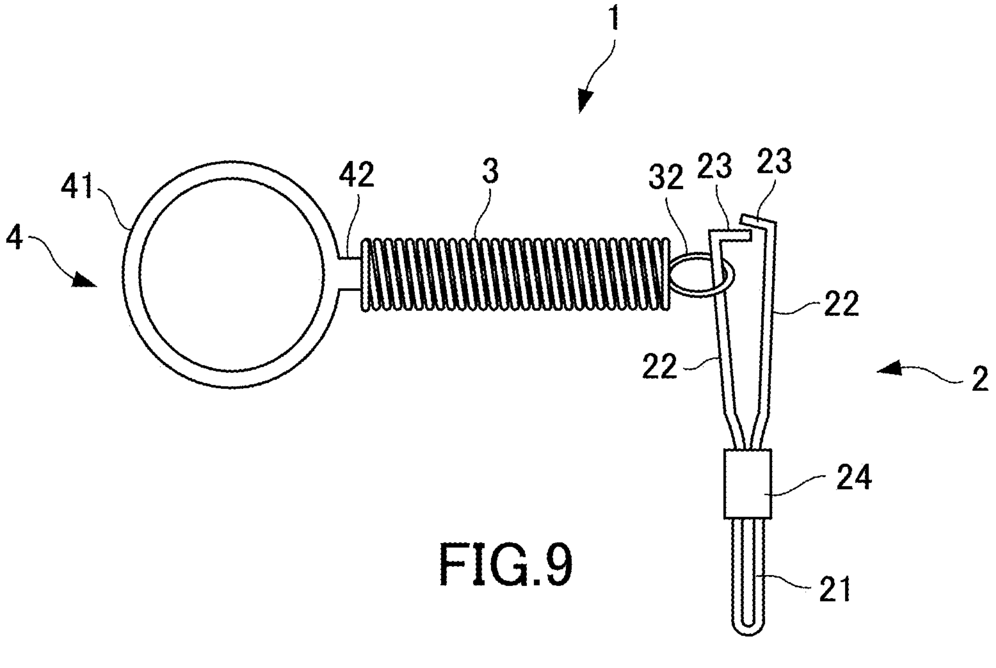
FIG. 9 is a diagram showing a state in which the arm portions of the clip body of the traction clip of FIG. 7 are closed.

As shown in FIGS. 7 to 9, the endoscopic traction clip 1 that can be used with the clip device 10 according to the present embodiment is generally configured with a clip body 2, a coil spring 3, and a loop member 4, and it is a clip with a spring that uses a coil spring 3 as a connection member that connects the clip body 2 and the loop member 4.

However, the coil spring 3 is an example of a connection member, and rubber, other elastic members, or members without elasticity may be used as the connection member. Further, the connection member may be omitted, and the loop member 4 may be directly connected (attached) to the clip body 2 without using the connecting member.

The clip body 2 includes a connecting plate portion (connecting portion) 21, a pair of arm plate portions (arm portion) 22 and a tightening ring 24. The connecting plate portion 21 has a substantially U-shaped bent shape, and an arm plate portion 22 is integrally formed so as to be continuous with each end of the U shape, and to open in a substantially V shape toward the tip end thereof.

The tightening ring 24 is a ring-shaped member that is slidably fitted on the connecting plate portion 21 on the base end side of the arm plate portion 22. The tightening ring 24 is a member to be slid using the clip device 10 (see FIGS. 1 to 6) that has the inner sheath (sheath) 12 and the a connection hook (engagement member) 11 which is disposed so as to be able to move forward and backward with respect to the inner sheath 12 and which is detachably connected (engaged) with the connection plate portion 21 (engageable). The tightening ring 24 is pushed by the tip of the inner sheath 12 to be slid so that the arm plate portion 22 is closed by retracting the connection hook 11 from the tip of the inner sheath 12, with the connection hook 11 connected to the connecting plate portion 21.

A claw portion 23 is integrally formed at the tip portion of each arm plate portion 22. The claw portion 23 is formed by being bent the tip end of the arm plate portion 22 toward the inside (that is, the closing direction). Each claw 23 has a recessed notch (not shown) in an intermediate portion of the tip thereof.

The connecting plate portion 21, the pair of arm plate portions 22, and the pair of claw portions 23, which collectively constitute the clip body 2, are formed by bending a single thin and elongated plate material. The plate thickness of the plate material forming the clip body 2 is not particularly limited, but is preferably 0.10 to 0.30 mm. As the plate material, a plate material having elasticity is preferable, and for example, stainless steel is used.

The arm plate portions 22 respectably have a base end portion 22*a* and a clip portion 22*b*, as shown in FIG. 8. The clip portion 22*b* of each arm plate portion 22 is formed with a penetrating portion 22*c*. These penetrating portions 22*c* are formed without impairing the desired strength of the arm plate portion 22 (clip portion 22*b*). Although the details will be described later, one of these penetrating portions 22*c* is also used to connect the coil spring 3 to the clip body 2.

The connecting plate portion 21 has a tightening ring 24 slidably fitted therein. The tightening ring 24 is substantially constituted by a cylindrical ring member. However, the tightening ring 24 may be constituted by a spring formed by winding a wire into a coil. The tightening ring 24 has the connecting plate portion 21 inserted through a guide hole on the inner side thereof, and is attached (outer fitting) to be axially movable (slidable) between the outer circumference of the connecting plate portion 21 and the outer circumference of the base end portion 22*a* of the arm plate portion 22.

As shown in FIG. 7 or 8, when the tightening ring 24 is arranged toward the rear side (connecting plate portion 21), the arm plate portion 22 is opened (opened legs) by its own elasticity. If necessary, as shown in FIG. 9, the arm plate portion 22 is closed (closed legs) by moving (sliding) the tightening ring 24 to a position closer to the tip end (base end portion 22*a*).

Figure 10A:
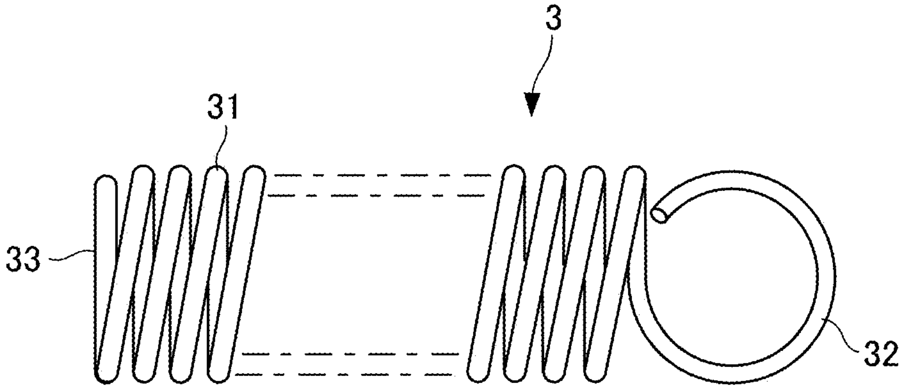
FIG. 10A is an enlarged configuration diagram of the coil spring of the traction clip of FIG. 7 and is a front view of the coil spring.
Figure 10B:
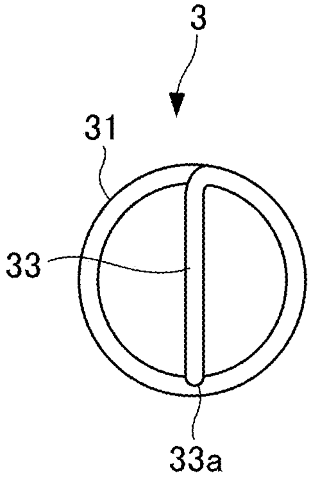
FIG. 10B is a view of the coil spring of FIG. 10A viewed from the loop member mounting side.

The coil spring 3 is a tension coil spring formed by winding a metal wire such as stainless steel. As shown in FIGS. 10A and 10B, coil spring 3 has a click hook portion 32 to be connected to clip body 2 at one end of the main body portion 31 formed by winding a metal wire, and a straight loop member hook portion 33 to attach (attach) loop member 4 at the other end of the main body portion 31. The clip hook portion 32 is formed by bending a portion corresponding to approximately one turn (or more than one turn) of one end of the metal wire (main body portion 31) wound in a substantially cylindrical shape at approximately 90 degrees with respect to a plane perpendicular to the axis of the main body portion 31. Alternatively, the clip hook portion 32 may be separately produced and fixed by welding to one end of the wound metal wire.

The loop member hook portion 33 is formed by bending a part of the other end of the main body portion 31 inward so as to draw a substantially D shape and forming it into a straight shape. The tip 33*a* of the straightly formed loop member hook portion 33 should extend to the wound metal wire (main body portion 31), as shown in FIG. 10(*b*), from the viewpoint of preventing the loop member 4 from passing through when the loop member 4 described below is connected. However, when the loop member 4 is fixed by adhesion or the like after being connected, the tip of the straight line portion formed in the straight shape does not have to reach the wound metal wire (main body portion 31).

Figure 11A:
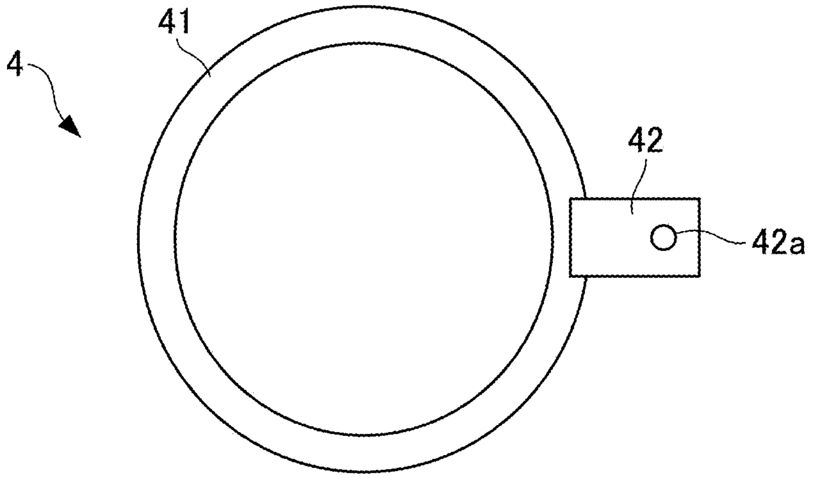
FIG. 11A is an enlarged view of the traction clip of FIG. 7, showing a plan view of the loop member.
Figure 11B:
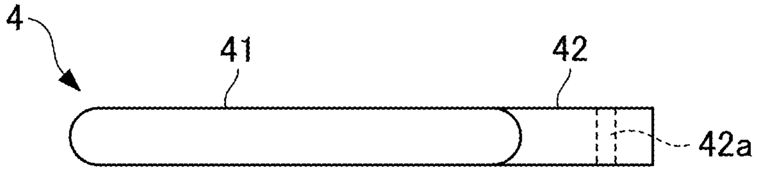
FIG. 11B is a front view of the loop member of FIG. 11A.

As shown in FIGS. 11A and 11B, the loop member 4 is constituted by a thermoplastic high molecular material molded part (in this embodiment, an injection molded product of a thermoplastic high molecular material) that is attached to a portion of the clip body 2 via a coil spring (connecting member) 3, and is comprising a loop portion 41 formed in a loop shape (endless shape) to which the connection hook (engagement member) 11 of the clip device 10 can be connected (engaged) to a part thereof, and an adapter portion 42 for connecting to the coil spring 3. In the present embodiment, the shape of the loop portion 41 is substantially an annular shape in a plan view, which has a uniform cross-sectional shape (substantially circular shape) over the entire circumference.

The loop portion 41 has flexibility to the extent that it can be accommodated in the distal end portion of the outer sheath 14 of the clip device 10, which will be described later, and the loop portion 41 is configured to be cut by shear force generated by the tip of the inner sheath 12 and the connection hook 11 by pulling the connection hook 11 from the tip of the inner sheath 12, in a state where the connection hook (engaging member) 11 is connected (engaged) to a part of the loop portion 41, using the clip device 10.

More specifically, in the loop portion 41, the shape (loop shape, cross-sectional shape), dimensions (loop diameter, cross-sectional diameter), material, molding method, molding conditions (molding temperature, pressure, and the like), and the like are set forth in relation to the inner diameter of the tip of the outer sheath 14, the inner diameter of the tip of the inner sheath 12, the configuration of the connection hook 11, and the like so as to have both the flexibility to the extent that it can be stored inside the outer sheath 14 and the brittleness to the extent that it can be cut by shearing force generated by the tip of the inner sheath 12 and the connection hook 11.

In this embodiment, the adapter portion 42 is a substantially rectangular plate like part integrally formed with the loop portion 41, and has a spring through hole 42*a* penetrating in a direction substantially perpendicular to the plate surface. The spring through hole 42*a* is a substantially circular hole into which the loop member hook portion (straight line portion) 33 of the coil spring 3 can be fitted. The inner diameter of the spring through hole 42 a is set to be equal to or slightly larger than the outer diameter of the loop member hook portion (straight line portion) 33 of the coil spring 3.

In the present embodiment, the adapter portion 42 is formed integrally with the loop portion 41 by injection molding, but the adapter portion 42 may be an adapter member independent of the loop portion 41 and joined to the loop portion 41. In this case, the adapter member is not limited to a substantially rectangular plate like the adapter portion 42, and may have other shapes and configurations as long as the function of connecting the coil spring 3 and the loop portion 41 can be realized.

The loop member 4 is connected to the coil spring 3 by inserting and placing the open end side of the adapter portion 42 inside the coil spring 3 (main body portion 31) to release elastic deformation of the loop member hook portion 33, while elastically deforming the loop member hook portion (straight line portion) 33 of the coil spring 3 outward (in the direction in which the tip portion 33*a* separates from the end portion of the body portion 31) as necessary, fitted (inserted) through the through hole 42*a* for the spring of the adapter portion 42. Thereby, the loop member 4 is connected (attached) to the coil spring 3. Thus, the work for connecting the adapter portion 42 to the coil spring 3 is easy, and the adapter portion 42 is prevented from passing through from the coil spring 3. In order to more reliably prevent the adapter portion 42 from passing through from the coil spring 3, the contact portion between the loop member hook portion 33 and the spring through hole 42*a* of the adapter portion 42 may be adhered.

As the material of the loop member 4, a thermoplastic polymer material is used. Specifically, thermoplastic resins such as polypropylene, polyethylene, polyamide, and polystyrene or thermoplastic elastomers such as polyolefin elastomers, polyamide elastomers, polystyrene elastomers, and polyurethane elastomers can be exemplified. The diameter (outer diameter) of the loop portion 41 can be about $\varphi^2$ to 6 mm, and the cross-sectional diameter of the loop portion 41 can be about 0.2 to 0.5 mm. The diameter of the spring through hole 42*a* can be about 0.1 to 0.3 mm.

Although the outer shape of the loop member 4 (loop portion 41) of the endoscopic traction clip 1 described above is substantially circular in a plan view, it is not limited to this, and may be oval, oblong, or polygonal (for example, rhombus), or a loop shape obtained by cutting a part of these and combining two or more of them. For example, it may have a loop shape composed of a semi-circular (arc-shaped) portion and a semi-rhombic (V-shaped) portion.

Further, the position of the adapter portion 42 with respect to the loop portion 41 may be anywhere since the loop portion 41 is substantially circular in the present embodiment, When the loop portion 41 has a flat shape such as an oval, it is preferably provided in one of the major axis directions, but it is preferably provided in one of the directions. When the loop portion 41 has a loop shape composed of a semi-circular (or semi-oval) portion and a semi-rhombic (V-shaped) portion, it is preferable to provide the adapter portion 42 at the vertex of the V-shaped portion.

Furthermore, although the cross-sectional shape of the loop portion 41 is substantially circular in this embodiment, it is not limited to this, and may be oval, oblong, or polygonal.

In addition, in the present embodiment, the loop portion 41 of the loop member 4 has a uniform substantially circular cross section over the entire circumference, but a part of the loop portion 41 of the loop member 4 may be made smaller in diameter than the other part, so that a weakened portion may be provided, thereby making it possible to cut the weakened portion with a weaker force than the other portions. By cutting such a weakened portion with the clip device 10, the cutting can be easily performed with a weaker force.

The endoscopic traction clip 1 as described above is mounted and accommodated in the tip portion (distal end portion) of the clip device 10, and the sheath portion (the inner sheath 12 and the outer sheath 14) of the clip device 10 is inserted into the lumen of the endoscope and guided to the living tissue to be treated.

<How to Use the Endoscope Traction Clip>

Next, a method for using the endoscopic traction clip 1 described above will be described. In the clip body 2, when the tightening ring 24 is fitted on the outer periphery of the connecting plate portion 21 near the base end portion 22*a*, a connecting hole 25 is formed in the connecting plate portion 21 having a U-shaped cross section (see FIG. 8, FIG. 12). The connection hook 11 of the clip device 10 (see FIG. 1) of the present embodiment is engaged with the connecting hole 25, and the connection hook 11 is retracted into the inner sheath 12, whereby the connection hook 11 is closed. The clip body 2 of the endoscopic traction clip 1 is attached to the tip of the inner sheath 12 (see FIG. 12).

Figure 13:
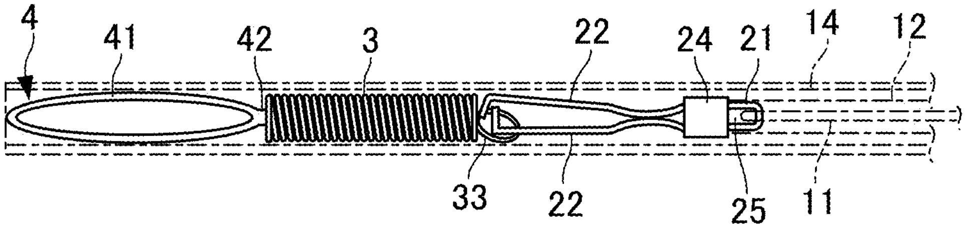
FIG. 13 is a diagram showing a state in which the traction clip of FIG. 7 is stored at the tip of the clip device.

In this state, the tip portion of the inner sheath 12 to which the endoscopic traction clip 1 (clip body 2, coil spring 3 and loop member 4) is connected is retracted into the outer sheath 14, as shown in FIG. 13, the entire endoscopic traction clip 1 (clip body 2, coil spring 3 and loop member 4) is accommodated inside the distal end portion of the outer sheath 14. In this state, the tightening ring 24 of the clip body 2 remains positioned on the connecting plate portion 21 and the arm plate portion 22 is closed by the action of the inner wall of the outer sheath 14. Further, the loop portion 41 of the loop member 4 is accommodated in the outer sheath 14 in an elastically deformed state by the action of the inner wall of the outer sheath 14.

Figure 12:
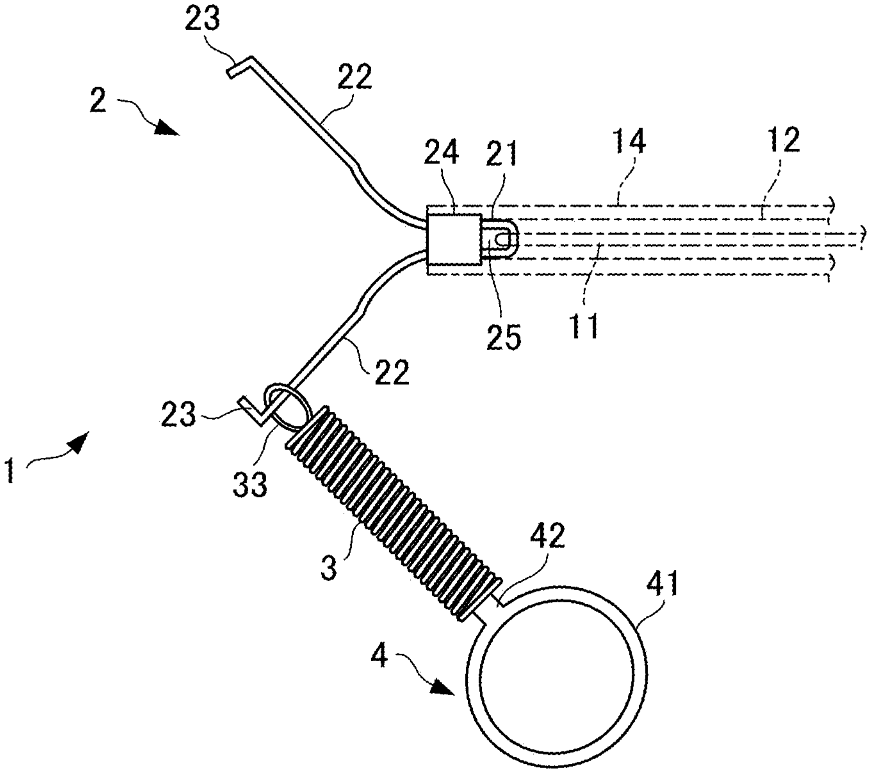
FIG. 12 is a diagram showing a state in which the traction clip of FIG. 7 is projected from the tip of the clip device.

Using an endoscope (not shown), the tip of the sheath portion of the clip device 10 to which the endoscopic traction clip 1 is attached is positioned in the vicinity of the living tissue to be incised (exfoliated). Next, by sliding the outer sheath 14 to the base end side, the endoscopic traction clip 1 is protruded from the distal end of the outer sheath 14. As a result, as shown in FIG. 12, the arm plate portion 22 is opened by its own elasticity, and the loop portion 41 of the loop member 4 returns to its original shape by its own elasticity.

Figure 14:
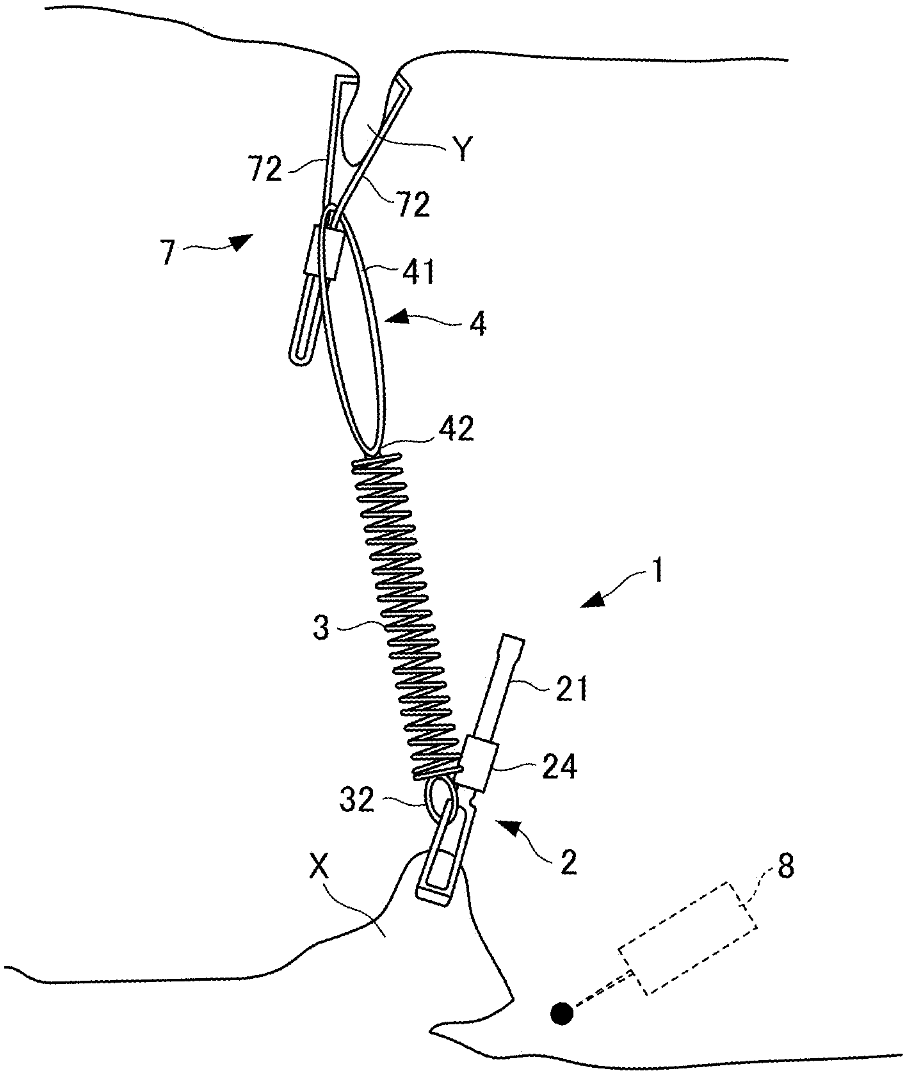
FIG. 14 is a diagram schematically showing a state in which part of a lesion is incised cut using the traction clip of FIG. 7.

With the arm plate portion 22 open, for example, as shown in FIG. 14, the arm plate portion 22 is positioned in the vicinity of the site (lesion) X to be excised (exfoliated) in the mucous membrane (living tissue). Next, by sliding the inner sheath 12 to the tip side with respect to the operation wire 13, the tightening ring 24 slides to the tip side of the arm plate portion 22. As a result, the arm plate portions 22 gradually close (they approach each other), and the mucous membrane on one side and the mucous membrane on the other side of the lesion X are pulled together.

By sliding the inner sheath 12 further toward the tip side with respect to the operation wire 13, the tightening ring 24 moves toward the clip portion 22*b* of the arm plate portion 22 (see FIG. 9), thereby clipping of the lesion X by the endoscopic traction clip 1 (the main body 2) is completed. In this state, by sliding the inner sheath 12 toward the proximal end side with respect to the operation wire 13, the connection hook 11 is pushed out from the distal end of the inner sheath 12 to open the legs, the clipping (engagement) of the endoscopic traction clip 1 (the clip body 2) by the connection hook 11 is released, thereby completing the clipping of the lesion X by the endoscopic traction clip 1 (clip body 2).

Next, once the clip device 10 is removed from the endoscope, another separately prepared clip (normal clip) 7 is attached to the tip of the clip device 10 (or a separately prepared clip device having the same configuration as the clip device 10), and convey the tip of the sheath portion of the clip device 10 to which the normal clip 7 is attached to the vicinity of an appropriate site (opposing site) Y that faces (opposes) the lesion X. As the ordinary clip 7, a clip having the same configuration as the clip main body 2 obtained by removing the coil spring 3 and the loop member 4 from the endoscopic traction clip 1 shown in FIGS. 7 to 9 can be used.

Next, the loop portion 41 of the loop member 4 is scooped up by one of the pair of arm plate portions 72 of the normal clip 7 (a part of the loop portion 41 is positioned between the pair of arm plate portions 72), stretching the coil spring 3, the normal clip 7 is clipped to the opposing site Y in the same manner as the above-described clipping of the lesion X by the clip body 2. As a result, the lesion X is pulled up (lifted) by the elastic force (tension) of the coil spring 3. After this state is established, an endoscopic electric knife 8 is inserted through the endoscope, and the perimeter of the lesion X is incised using the endoscopic electric knife 8. Since the lesion X is lifted by the elastic force (tension) of the coil spring 3 from the part exfoliated by the incision, the entire circumference of the lesion X can be easily and reliably incised, without the part exfoliated by the incision of the lesion X does not obstructing the field of vision or interfering with the manual procedure.

Figure 15:
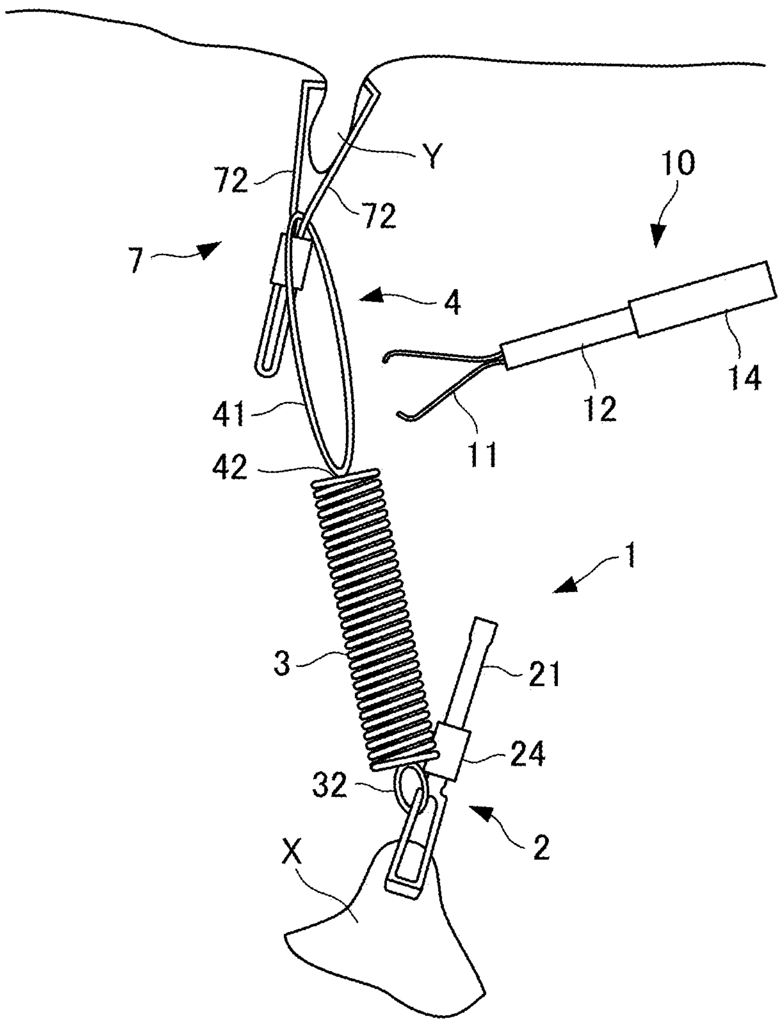
FIG. 15 is a diagram schematically showing a state in which incision of the part of the lesion site following

Next, as shown in FIG. 15, after the excision of the lesion X is completed and the endoscopic electric knife 8 is removed from the endoscope, the tip of the clip device 10 with no clips attached (connected) (or a separately prepared clip device having the same configuration as the clip device 10) is positioned in the vicinity of the loop portion 41 of the loop member 4 being towed, and the connection hook 11 is protruded from the tip of the inner sheath 12 to open legs. In this state, as shown in FIG. 16A, the position is finely adjusted so that an appropriate portion of the loop portion 41 can be clipped.

Next, the inner sheath 12 is pushed on the tip side with respect to the operation wire 13, so that the connection hook 11 is closed, and an appropriate part of the loop portion 41 is clipped by the connection hook 11 as shown in FIG. 16B, the loop portion 41 is brought into contact with the tip of the inner sheath 12. After that, as shown in FIG. 16C, by sliding the operation wire 13 toward the base end side with respect to the inner sheath 12 to retract the operation wire 13 in, the appropriate part of the loop portion 41 is cut by the shear forces generated by the tip of the inner sheath 12 and the connection hook 11. After the loop portion 41 is cut, the lesion X can be clipped together with the traction clip 1 by the connection hook 11 of the clip device 10 or the endoscopic clipping forceps or the like and extracted from the body.

FIG. 17 shows the closed state between the pair of claw portions **11*a*1 and 11*b*1 when the connection hook 11 is retracted into the inner sheath 12 in the clip device 10 of this embodiment. In the accommodated state of the pair of arm portions 11*a* and 11*b* in the leg closed state shown in FIG. 17, the gap (separation distance d) between the claw portions 11*a*1 and 11*b*1 of the arm portions 11*a* and 11*b* is very close, 0.15 mm or less. In this state, the loop member 4 is stretched to the state indicated by the dotted line in FIG. 17 while maintaining a cross-sectional diameter larger than the separation distance between the claw portions 11*a*1 and 11*b*1, so that it does not pass between the claw portions 11*a*1 and 11*b*1. As a result, by retracting the connection hook 11 and the loop member 4 further into the inner sheath 12 from the accommodated state as shown in FIG. 17, a tension can be applied to the loop member 4 in the state where the loop member 4 does not pass through between the claw portions 11*a*1 and 11*b*1 of the pair of arm portions 11*a* and 11*b*, so that the loop member 4** can be reliably cut.

The clip device 10 according to the present embodiment can reduce the cost required for treatment, because there is no need to separately prepare a cutting tool for cutting the loop member 4, since the clip device 10 according to this embodiment can cut the loop member 4 (loop portion 41) of the endoscopic traction clip 1, while retracting the loop portion 41 into the inner sheath 12, in the state where a part of the loop member 4 is clipped between the claw portions **11*a*1 and 11*b*1 of the pair of arm portions 11*a* and 11*b* of the connection hook 11**.

In particular, the gap (d) at the closest portion between the claw portions **11*a*1 and 11*b*1 of the arms 11*a* and 11*b* at the time when the pair of arm portions 11*a* and 11*b* of the connection hook 11 are buried in the inner sheath 12 and closed is set to a specified value, for example, 0.15 mm, which prevents the loop member 4 (loop portion 41), which is clipped between the claw portions 11*a*1 and 11*b*1, from passing through in the clip device 10 of the present embodiment. As a result, the clip device 10 according to the present embodiment can reliably shear the loop member 4 (loop portion 41), while securely clipping the loop member 4 (loop portion 41) between the claw portions 11*a*1 and 11*b*1 of the pair of arm portions 11*a* and 11*b* of the connection hook 11**.

<Operation According to the Present Embodiment>

The operation of the present embodiment will be described below.

The clip device 10 according to the present invention comprises: a tubular sheath (inner sheath 12 and outer sheath 14); an operation portion 18 provided at a proximal end of the sheath and allows an operation wire 13 inserted through the sheath to slide with respect to the sheath; and a connection hook 11 constituted by an elastic body having a pair of arm portions **11*a*, 11*b* attached at a distal end of the operation wire 13 and arranged so as to open each other in a substantially V shape as it goes to its tip, the connection hook 11 protruding from the distal end of the inner sheath 12 to open the pair of arm portions 11*a*, 11*b* by its own elasticity by sliding the inner sheath 12 towards a proximal side with respect to the operation wire 13, the connection hook 11 being buried in the distal end of the inner sheath 12 to close the pair of arm portions 11*a*, 11*b* by sliding the sheath towards the distal end side with respect to the operation wire 13, wherein the connection hook 11 has a pair of claw portions 11*a*1, 11*b*1 at the tip of each of the pair of arm portions 11*a*, 11*b* that are bent in the closing direction and that can be pulled into the inner sheath by clipping a part of the endoscopic traction clip 1 clip to which a loop member 4 is connected in accordance with the operation of pulling in the sheath, a gap at the closest portion between the pair of claw portions 11*a*1, 11*b*1 when the pair of arm portions 11*a*, 11*b* are buried in the inner sheath 12 and closed has a specified value that prevents the loop member 4 from passing through, when a part of the loop member 4 is clipped between the pair of claw portions Hal, 11*b*1**.

By this configuration, the clip device 10 according to the present embodiment prevents the loop member 4 from passing through in the process of accommodating a portion of the loop member 4 between the pair of claw portions **11*a*1 and 11*b*1 and retracting it into the inner sheath 12, so that the loop member 4** can be reliably cut.

Further, in the clip device 10 according to the present embodiment, the claw portion (first claw portion) **11*a* of the connection hook 11, which is the claw portion of one arm portion of the pair of arm portions 11*a* and 11*b*, is bent from its base end portion 11*a*2 by a predetermined diameter, the other claw portion (second claw portion) 11*b* of the connection hook 11, which is the claw portion of the other arm portion 11*b*1, is bent from its base end portion 11*b*2 to a diameter longer than the claw portion 11*a* and larger than the predetermined diameter, the pair of arm portions 11*a*, 11*b* are closed in such a manner that the claw portion 11*b*1 covers the claw portion 11*a*1 from the outside, in a state of being buried in the inner sheath 12, the closest portion is formed between the protruding end portion 11*a*3 of the claw portion 11*a*1 and the region 11*b*4 between the protruding end portion 11*b*3 of the claw portion 11*b*1 and the base end portion 11*b*2**.

By this configuration, the clip device 10 according to the present embodiment can prevent the first claw portion and the second claw portion from interfering with each other when the pair of arm portions **11*a* and 11*b* are buried in the inner sheath 12 and the legs are closed, so that the loop member 4 can be reliably cut without interfering movement each other when the pair of arm portions 11*a* and 11*b* are buried in the inner sheath 12** and closed.

Further, in the clip device 10 according to the present embodiment, the specific value is 0.15 mm or less. By this configuration, the clip device 10 according to the present embodiment can reliably prevent the loop member 4 from passing through and cut the loop member 4, even in the situation where the loop member 4 is extended by the tension applied to the loop member 4 in the process of retracting a part of the loop member 4 between the pair of claw portions 11*a*1 and 11*b*1 into the inner sheath 12.

In addition, in the clip device 10 of the present embodiment, the connection hook 11 is configured to releasably connect a medical clip (endoscope traction clip 1) that clips body tissue and is indwelled.

By this configuration, the clip device 10 of the present embodiment can be preferably used as a clip device that is an endoscopic treatment tool provided with the connection hook 11 that releasably connects the medical clip that is indwelled by clipping body tissue as an opening/closing portion.

The above-described embodiments describe examples in which the endoscopic treatment tool are applied to the clip device, but the present invention is not limited to the clip device, and the present invention can be broadly applied to an endoscopic treatment tool comprising an opening/closing portion, constituted by an elastic body having a pair of arm portions arranged so as to spread each other in a substantially V shape as it goes to its tip, protruding from the distal end of the sheath to open the pair of arm portions by its own elasticity by sliding the sheath towards a proximal side with respect to the operation wire, and being buried in the distal end of the sheath to close the pair of arm portions by sliding the sheath towards the distal end side with respect to the operation wire.

More specifically, for example, a snare ligating device that includes a connection hook that connects an indwelling snare and ligates body tissue as the opening/closing portion, a forceps device that includes forceps that clips body tissue as the opening/closing portion, and bipolar type high-frequency device with a high-frequency electrode that opens and closes as the opening/closing portion, and a ligature cutting tool that cuts the ligature suturing a defective part of body tissue by clipping the ligature with the opening/closing portion and retracting the ligature into the sheath.

The embodiments described above are described to make it easy to understand the present invention, and are not described to limit the present invention. Therefore, each element disclosed in the above-described embodiment is meant to include all design changes and equivalents that fall within the technical scope of the present invention.

EXPLANATION OF REFERENCE NUMERALS

1 Endoscopic Traction Clip (Clip)
4 Loop Member
10 Clip Device (Endoscopic Treatment tool)
11 Connection Hook (Opening/Closing Portion)
11*a*, 11*b* A Pair of Arm Portions (Arm Portions)
11*a*1 Claw Portion (First Claw Portion)
11*a*2 Base End Portion of the First Claw Portion (Base End Portion)
11*a*3 Protruding End Portion of the First Claw (Protruding End Portion)
11*b*1 Claw Portion (Second Claw Portion)
11*b*2 Base End of the Second Claw Portion (Base End Portion)
11*b*3 Protruding End of the Second Claw (Protruding End Portion)
11*b*4 Region between the Protruding End Portion and the Base End Portion of the Second Claw Portion (Region)
12 Inner Sheath (Sheath)
13 Operation Wire
14 Outer Sheath
18 Operation Portion

What is claimed is:

1. An endoscopic treatment tool, comprising:
a tubular sheath;
an operation portion directly connected to a proximal end of the sheath, the operation portion configured to allow an operation wire inserted through the sheath to slide with respect to the sheath; and
an opening/closing portion constituted by an elastic body having a pair of arm portions attached at a distal end of the operation wire and arranged so as to open each other in a substantially V shape toward a tip of the pair of arm portions,
the opening/closing portion protrudes from the distal end of the sheath to open the pair of arm portions by an elasticity of the pair of arm portions by sliding the sheath towards a proximal side with respect to the operation wire,
the opening/closing portion is buried in the distal end of the sheath to close the pair of arm portions by sliding the sheath distally with respect to the operation wire, wherein
the opening/closing portion has a pair of claw portions at the tip of each of the pair of arm portions that are bent in a closing direction and that can pull a clip connected to a loop member into the sheath by holding a part of the clip during a movement to bury the opening/closing portion in the sheath,
a gap at a closest portion between the pair of claw portions when the pair of arm portions are buried in the sheath and closed, wherein the gap has a specified value that prevents the loop member from passing through, when a part of the loop member is clipped between the pair of claw portions,
a first claw portion of the opening/closing portion, which is the claw portion of one arm portion of the pair of arm portions, is bent from a base end by a predetermined radius of curvature,
a second claw portion of the opening/closing portion, which is the claw portion of the other arm portion, is bent from a base end portion by a radius of curvature longer than the first claw portion and larger than the predetermined radius of curvature,
the pair of arm portions are closed in such a manner that the second claw portion covers the first claw portion from the outside while in a state of being buried in the sheath such that a distal-most portion of the second claw portion extends past a distal-most portion of the first claw portion,
the closest portion is formed between a protruding end portion of the first claw portion and the region between a protruding end portion of the second claw portion and the base end portion.

2. The endoscopic treatment tool according to claim 1, wherein the specified value is 0.15 mm or less.

3. The endoscopic treatment tool according to claim 1, wherein the opening/closing portion is a connection hook that releasably connects the clip indwelled while clipping body tissue.

* * * * *